US007001241B2

(12) United States Patent
Gorringe et al.

(10) Patent No.: US 7,001,241 B2
(45) Date of Patent: Feb. 21, 2006

(54) DUAL BREAST PAD AND BIB APPARATUS

(76) Inventors: Heather Gorringe, 21 N. Campbell, Nampa, ID (US) 83687; Heidi Bench, 510 N. Wilson, Oakley, ID (US) 83346; Brandi Raass, 2413 E. Nutmeg La., Nampa, ID (US) 83686; Travis Bruce Mitchell, 2104 S. 100 East, Oakley, ID (US) 83346; Bruce N. Mitchell, 2104 S. 100 East, Oakley, ID (US) 83346; Elaine Mitchell, 2104 S. 100 East, Oakley, ID (US) 83346

( * ) Notice: Subject to any disclaimer, the term of this patent is extended or adjusted under 35 U.S.C. 154(b) by 0 days.

(21) Appl. No.: 10/703,096

(22) Filed: Nov. 6, 2003

(65) Prior Publication Data

US 2004/0154068 A1 Aug. 12, 2004

Related U.S. Application Data

(60) Provisional application No. 60/424,391, filed on Nov. 6, 2002.

(51) Int. Cl.
*A41D 3/00* (2006.01)

(52) U.S. Cl. .......................................... 450/81; 450/37

(58) Field of Classification Search ............ 450/37–39, 450/55–57, 81; 2/46, 53, 56, 58, 267, 104; 128/890; 604/385, 385.01, 385.07, 385.201, 604/385.06

See application file for complete search history.

(56) References Cited

U.S. PATENT DOCUMENTS 1,217,441 A 2/1917 Guinzburg
3,934,593 A 1/1976 Mellinger
4,221,221 A * 9/1980 Ehrlich ....................... 604/386
4,324,237 A 4/1982 Buttaravoli
4,674,510 A * 6/1987 Sneider ....................... 450/57
4,992,074 A 2/1991 Diaz
5,086,763 A 2/1992 Hathman
5,449,340 A 9/1995 Tollini
5,569,230 A * 10/1996 Fisher et al. ........... 604/385.06
5,582,605 A * 12/1996 Lepie .................... 604/385.06
5,755,232 A * 5/1998 Kalt ........................... 128/845
5,919,180 A 7/1999 Raimondo
5,960,471 A * 10/1999 Burton ............................ 2/48
6,004,307 A * 12/1999 Colon et al. ........... 604/385.06
6,074,272 A * 6/2000 Hebert ........................ 450/37
6,083,079 A 7/2000 Pearson
6,257,952 B1 7/2001 Valentin
6,361,398 B1 3/2002 Knapp
6,645,042 B1 * 11/2003 Davis .......................... 450/88

FOREIGN PATENT DOCUMENTS

GB 2 197 590 A 5/1988

* cited by examiner

*Primary Examiner*—Gloria M. Hale
(74) *Attorney, Agent, or Firm*—Christensen O'Connor Johnson Kindness PLLC

(57) ABSTRACT

The present invention provides a dual breast pad and nursing bib apparatus comprising a cup-shaped base flap and a nursing flap, wherein the nursing flap is hingedly coupled to the cup-shaped base flap, and wherein the nursing flap may be rotated between a first closed position and a second bib position. In some embodiments, the apparatus comprises adhesive areas on the cup-shaped base flap and/or on the nursing flap. In some embodiments, the apparatus further comprises adhesive flaps hingedly coupled to the cup-shaped base flap.

16 Claims, 3 Drawing Sheets

4
16
10
20
24
12
22
14
14
18
4

14
20
10
22
12
16

DUAL BREAST PAD AND BIB APPARATUS

CROSS-REFERENCE TO RELATED APPLICATION

This application claims the benefit of U.S. Provisional Application No. 60/424,391, filed Nov. 6, 2002.

FIELD OF THE INVENTION

The present invention relates generally to undergarments and, more particularly, to nursing pads.

BACKGROUND OF THE INVENTION

During breastfeeding, leaking of the breasts is a common occurrence. It is the body's way of preventing engorgement and relieving the feeling of fullness nursing moms get in their breasts. Every breastfeeding woman is different—while some mothers never leak, others can barely keep their nursing tops dry. To soak up the fluids leaked from the breast, absorbent nursing pads are applied in the vicinity of the nipple. However, the pad must be removed prior to breastfeeding. During breastfeeding, fluids are often spilled, wetting the woman's breast and surrounding clothing if precautions are not taken, such as placing a bib underneath the breast. And, even if such a bib is placed underneath the breast, a large portion of the breast is exposed and may become wetted. Further still, a woman must carry both nursing pads and bibs. Further still yet, the bib must be disposed of or stored and later washed after feeding, increasing the cost and inconvenience of breastfeeding. Thus, there exists a need for a device that performs as both a nursing pad and a bib, which may remain in place during breastfeeding to absorb any fluids leaked during feeding, thereby eliminating the need for a separate bib.

SUMMARY OF THE INVENTION

The present invention provides a dual breast pad and nursing bib apparatus comprising a cup-shaped base flap and a nursing flap, wherein said nursing flap is hingedly coupled to said cup-shaped base flap, and wherein said nursing flap may be rotated between a first closed position and a second bib position. In some embodiments, the apparatus comprises adhesive areas on the cup-shaped base flap and/or on the nursing flap. In some embodiments, the apparatus further comprises adhesive flaps hingedly coupled to said cup-shaped base flap. In further embodiments, the cup-shaped base flap comprises a self-supporting, contoured shape. In still further embodiments, the apparatus further comprises an attached wipe containing a cleaning agent, a medicinal agent or a skin benefit agent. In yet still further embodiments, the apparatus is disposable.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Unless specifically defined herein, all terms used herein have the same meaning as they would to one skilled in the art of the present invention.

Generally described, the present invention provides a strapless dual breast pad and nursing bib apparatus comprising a cup-shaped base flap and nursing flap, wherein said nursing flap is hingedly coupled to said cup-shaped base flap and wherein said nursing flap may be rotated between a first closed position and a second bib position.

The dual breast pad and nursing bib apparatus may be used by any woman who is nursing an infant. The apparatus is useful both for absorbing excess lacteal fluid and for absorbing any fluids leaked during breast feeding, thereby eliminating the need for a separate bib. The apparatus may be disposed of after a feeding session and a new one installed, or may be reused.

Figure 1:
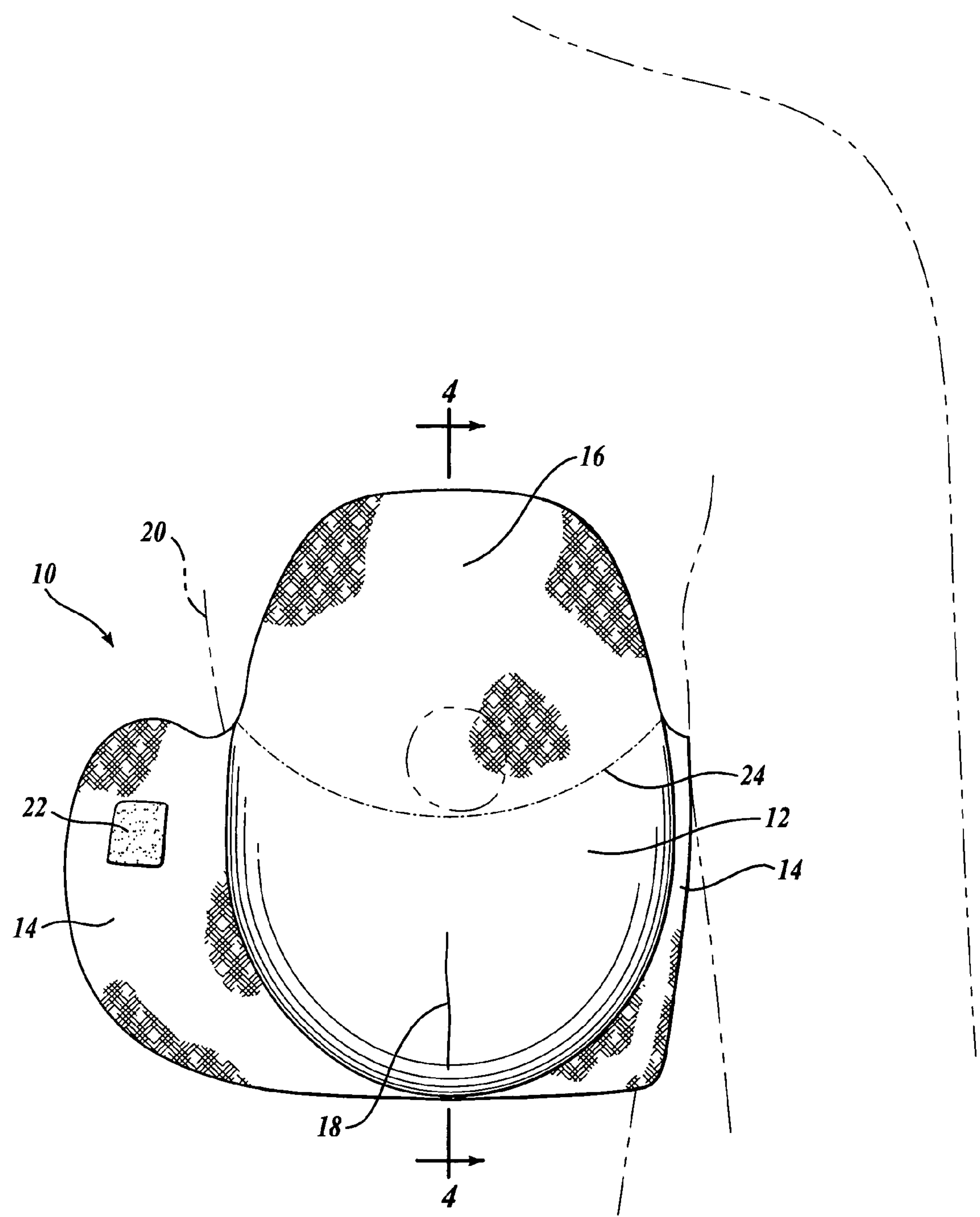
FIG. 1 is a plan view of one embodiment of a dual breast pad and bib apparatus formed in accordance with the present invention.
Figure 3:
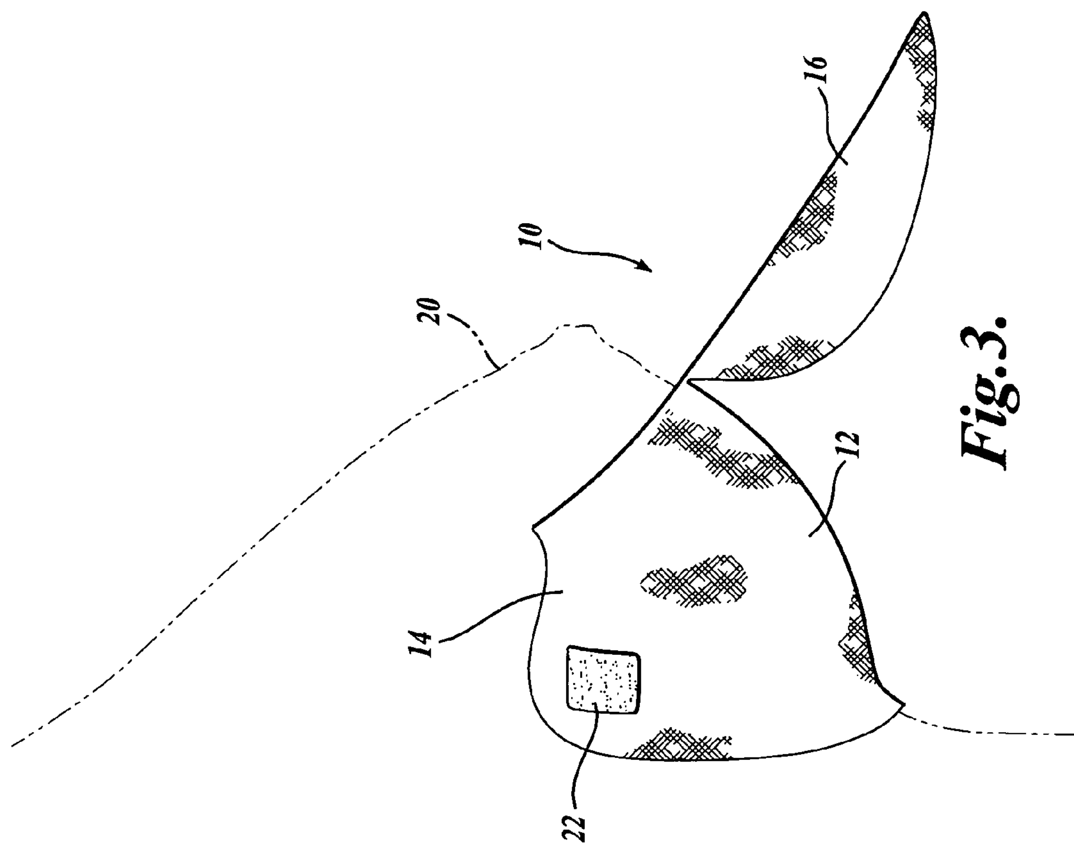
FIG. 3 is a side view of the dual breast pad and bib apparatus of FIG. 1 depicted donned upon a breast of a woman, wherein the nursing flap of the dual breast pad and bib apparatus is shown in a folded down position to permit access to the nipple.
Figure 2:
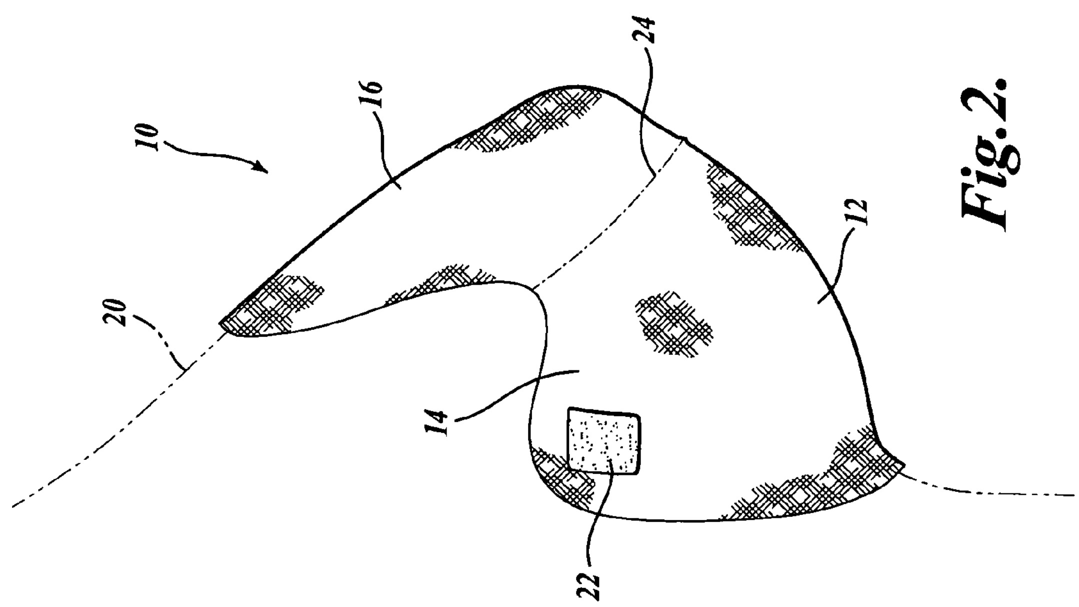
FIG. 2 is a side view of the dual breast pad and bib apparatus of FIG. 1 depicted donned upon a breast of a woman, wherein a nursing flap of the dual breast pad and bib apparatus is shown in an upright position.

Referring to FIGS. 1 and 2, a dual breast pad and nursing bib apparatus 10 is shown. The breast pad and nursing bib apparatus 10 includes a nursing flap 16 hingedly coupled 24 to a base flap 12. As best shown in FIGS. 2 and 3, the base flap 12 extends outward from a hinge 24 disposed between the base flap 12 and the nursing flap 16 a first distance. The nursing flap 16 extends outward from the hinge 24 a second distance. As shown in FIGS. 2 and 3, the first distance is substantially equal to or less than the second distance such that the nursing flap 16 extends further outward from the hinge 24 than the cup-shaped base flap 12. Thus, as best shown in FIG. 3, when the nursing flap 16 is folded down, the nursing flap 16 extends over the underlying base flap 12 to cover and protect the base flap 12.

Optionally, a pair of adhesive wings 14 are hingedly coupled on opposite sides of base flap 12. When worn by a woman, adhesive wings 14 are applied to the sides of breast 20, holding the breast pad and nursing bib apparatus 10 in place, with the base flap 12 positioned underneath breast 20 and nursing flap 16 in an upright position, covering the nipple. In this configuration, the breast pad and bib apparatus 10 absorbs any leakage that may occur from the breast 20, provides support to the breast 20, and obscures the shape of the nipple from showing through any garment. The size of apparatus 10 can be varied to accommodate wearers with different cup sizes. As shown in FIG. 1, in some embodiments cup-shaped base flap 12 may be formed into a contoured, self-supporting shape by adding pleat 18 to base flap 12.

Referring to FIGS. 2 and 3, when a woman wishes to breastfeed her baby, the nursing flap 16 is folded down along hinge 24, allowing the baby access to the nipple. The nursing flap 16, in its folded down position, acts as a bib, absorbing any fluids spilled during feeding. The breast pad and bib apparatus 10 may then be disposed of after the completion of the feeding session and a new one installed, or alternately returned to the upright position. A wipe 22 may be attached to apparatus 10 to aid in post feeding clean-up.

Figure 4:
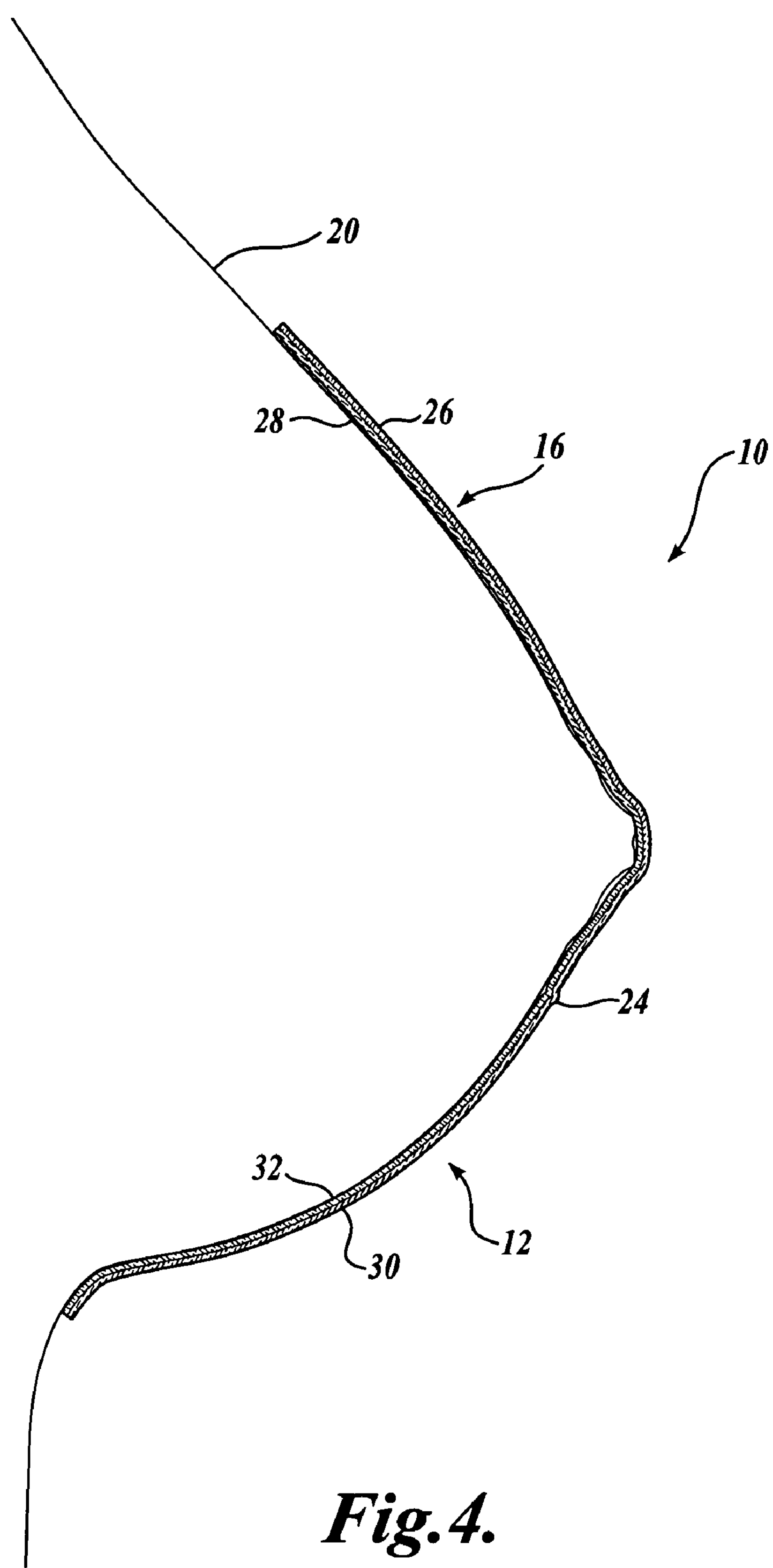
FIG. 4 is a cross-sectional view of the dual breast pad and bib apparatus of FIG. 1 depicted donned upon a breast of a woman, wherein the inside and outside surfaces of the nursing flap and the cup-shaped base flap are shown.

Referring to FIG. 4, which is a cross-sectional view of FIG. 1, the nursing flap 16 is shown in the upright position hingedly coupled 24 to base flap 12. The front side 28 of nursing flap 16 faces breast 20 and the back side 26 of nursing flap 16 faces the woman's clothing. With continued reference to FIG. 4, front side 32 of base flap 12 faces breast 20 and the back side 30 of base flap 12 faces the woman's clothing. In some embodiments of apparatus 10, front side 32 of base flap 12 and front side 28 of nursing flap 16 comprise absorbent material. The absorbent material may be any absorbent material that is flexible and absorbs liquid. Illustrative examples of suitable absorbent material for use in apparatus 10 include cotton sheath, cotton flannel, nylon, polyester, absorbent fibers, including one or both of natural and synthetic fibers, a fluffy pulp and the like. In some embodiments, front side 32 and front side 28 comprise the same absorbent material, and in some embodiments front side 32 and front side 28 comprise different absorbent material. In some embodiments apparatus 10 comprises elastic fabric.

Referring again to FIG. 4, in some embodiments of apparatus 10, back side 30 of base flap 12 and back side 26 of nursing flap 16 comprise water impermeable material to prevent leakage. Water impermeable material suitable for use in the apparatus includes any flexible material that is substantially water impermeable. Illustrative examples of suitable water impermeable materials include a thin plastic film, a synthetic resin film or other flexible liquid-impermeable material. Back side 30 and back side 26 may optionally be composed of a micro-porous "breathable" material which permits water vapor to escape from front side absorbent material 28 and 32 while still preventing liquid from passing through the back side. For example, the breathable backside may be composed of a microporous polymer film or a nonwoven fabric which has been coated or otherwise treated to impart a desired level of liquid impermeability.

As indicated above, in some embodiments apparatus 10 includes adhesive areas which are used to adhere apparatus 10 to breast 20. Referring to FIG. 4, adhesive areas may be present on a region of front side 28 and/or front side 32. Alternatively, in some embodiments, base flap 12 further comprises adhesive flaps 14 as shown in FIGS. 1, 2 and 3. Adhesion to breast 20 may be accomplished using any adhesive suitable for contact with the human skin. For example, adhesion may be accomplished using a two-sided tape with a body side adhesive on one side and a fabric side adhesive on the other side. The body side adhesive may be detachably covered with a protective paper. Body side adhesive is preferably a hypoallergenic, pressure sensitive, acrylate adhesive that is non-toxic and reduces irritation of the skin of a user.

As also indicated above, in some embodiments of apparatus 10, a packaged, folded wipe 22 may be attached for clean-up after feeding as shown in FIG. 1. Wipe 22 may contain an agent selected from the group consisting of a cleaning agent, a medicinal agent and a skin benefit agent, and combinations thereof. Suitable cleaning agents include, for example, lanolin based cleaning agents. Suitable medicinal agents include, for example, antimicrobial actives, antifungal actives, antiseptic actives and astringents. Suitable skin benefit agents include any composition that is useful for improving the skin health of a woman's breast and nipple skin which often becomes dry and cracked during breast-feeding. Illustrative examples of skin benefit agents include emulsions, lotions, creams, salves and the like.

While the preferred embodiment of the invention has been illustrated and described, it will be appreciated that various changes can be made therein without departing from the spirit and scope of the invention.

What is claimed is:

1. A strapless breast pad and nursing bib apparatus comprising:

a cup-shaped base flap for cupping and supporting a lower portion of a breast, the cup-shaped base flap having an adhesive coupled thereto for adhering the cup-shaped base flap to the breast; and a nursing flap;

wherein said nursing flap is hingedly coupled to said cup-shaped base flap by a hinge, wherein said nursing flap may be rotated between a first closed position and a second bib position about the hinge, and wherein the cup-shaped base flap extends outward from the hinge a first distance and wherein the nursing flap extends outward from the hinge a second distance, wherein the first distance is substantially equal to or less than the second distance such that the nursing flap extends further outward from the hinge than the cup-shaped base flap.

2. The apparatus according to claim 1, wherein said cup-shaped base flap and said nursing flap have a front side which faces a breast and a back side which faces a woman's clothing, said front side comprising an absorbent material and said back side comprising a liquid impermeable material.

3. The apparatus according to claim 2, wherein said back side comprises a breathable material.

4. The apparatus according to claim 2, wherein said front side of said cup-shaped base flap comprises adhesive areas.

5. The apparatus according to claim 2, wherein said front side of said nursing flap comprises adhesive areas.

6. The apparatus according to claim 1, further comprising adhesive flaps having the adhesive disposed thereon, the adhesive flaps hingedly coupled to said cup-shaped base flap.

7. The apparatus according to claim 4, 5 or 6 wherein said adhesive is hypo-allergic.

8. The apparatus according to claim 1, wherein said cup-shaped base flap comprises a self-supporting, contoured shape.

9. The apparatus according to claim 1, wherein said nursing flap is of sufficient size and shape to extend underneath the breast in a self-supporting bib position.

10. The apparatus according to claim 1, wherein said apparatus comprises an elastic fabric.

11. The apparatus according to claim 1 further comprising an attached wipe.

12. The apparatus according to claim 11, wherein said attached wipe contains an agent selected from the group consisting of a cleaning agent, a medicinal agent and a skin benefit agent and combinations thereof.

13. The apparatus according to claim 1, wherein said apparatus is disposable.

14. A strapless breast pad and nursing bib apparatus comprising:

a cup-shaped base flap for cupping and supporting a lower portion of a breast, the cup-shaped base flap having an adhesive coupled thereto for adhering the cup-shaped base flap to the breast; and a nursing flap having an upper portion free of an adhesive for attaching the nursing flap to the breast;

wherein said nursing flap is hingedly coupled to said cup-shaped base flap by a hinge, wherein said nursing flap may be rotated between a first closed position and a second bib position.

15. The apparatus of claim 14, wherein the cup-shaped base flap extends outward from the hinge a first distance and wherein the nursing flap extends outward from the hinge a second distance, wherein the first distance is substantially equal to or less than the second distance such that the nursing flap extends further outward from the hinge than the cup-shaped base flap.

16. The apparatus of claim 15, further comprising adhesive flaps having the adhesive disposed thereon, the adhesive flaps hingedly coupled to said cup-shaped base flap.

* * * * *